(12) United States Patent
Lee

(10) Patent No.: US 10,149,738 B2
(45) Date of Patent: *Dec. 11, 2018

(54) APPARATUS FOR APPLYING CORRECTIVE FORCES TO SHAPE PALATE

(71) Applicant: Sue S. Lee, Framingham, MA (US)

(72) Inventor: Sue S. Lee, Framingham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/444,502

(22) Filed: Feb. 28, 2017

(65) Prior Publication Data

US 2017/0165031 A1   Jun. 15, 2017

Related U.S. Application Data

(63) Continuation of application No. 14/747,121, filed on Jun. 23, 2015, now Pat. No. 9,615,896, which is a continuation of application No. 13/233,283, filed on Sep. 15, 2011, now Pat. No. 9,089,385.

(51) Int. Cl.
| | |
|---|---|
| *A61C 3/00* | (2006.01) |
| *A61C 7/10* | (2006.01) |
| *A61C 7/20* | (2006.01) |
| *A61C 7/14* | (2006.01) |
| *A61C 7/18* | (2006.01) |

(52) U.S. Cl.
CPC ............. *A61C 7/10* (2013.01); *A61C 7/145* (2013.01); *A61C 7/18* (2013.01); *A61C 7/20* (2013.01)

(58) Field of Classification Search
CPC .. A61C 7/10; A61C 7/145; A61C 7/18; A61C 7/20
See application file for complete search history.

(56) References Cited

U.S. PATENT DOCUMENTS

| | | | | |
|---|---|---|---|---|
| RE35,170 E | * | 3/1996 | Arndt ...................... | A61C 7/00 |
| | | | | 433/18 |
| 2009/0047614 A1 | * | 2/2009 | Fathianathan et al. .. | A61C 7/08 |
| | | | | 433/6 |

* cited by examiner

*Primary Examiner* — George Manuel
(74) *Attorney, Agent, or Firm* — Mintz Levin Cohn Ferris Glovsky and Popeo, P.C.; Kongsik Kim; Derek E. Constantine

(57) ABSTRACT

An orthodontic apparatus for installation in a patient's mouth is disclosed. The orthodontic apparatus includes a first extension wire, a second extension wire, and a palatal archwire. Each of the first and second extension wires includes a proximal portion and a distal portion. The proximal and distal portions and the palatal archwire are manipulatable to apply corrective buccal, labial, and transverse forces on the patient's dento-alveolar complex (DAC), to correct the shape of the patient's palate.

13 Claims, 8 Drawing Sheets

APPARATUS FOR APPLYING CORRECTIVE FORCES TO SHAPE PALATE

CROSS-REFERENCE TO RELATED APPLICATIONS

The present application is a continuation application claiming priority, under 35 U.S.C. § 120, to U.S. patent application Ser. No. 14/747,121 filed on Jun. 23, 2015, which is a continuation application claiming priority, under 35 U.S.C. § 120, to U.S. patent application Ser. No. 13/233,283 filed Sep. 15, 2011. The applications are incorporated herein by reference.

TECHNICAL FIELD

The invention relates to methods and devices for applying corrective forces within a patient's mouth, and more particularly to applying transverse, buccal, and labial forces to correct a patient's palate by use of a shaping device.

BACKGROUND INFORMATION

A palatal arch expander assembly is described in U.S. Pat. No. 5,816,800. And various palatal and other orthodontic devices are available commercially from various sources such as an orthodontic laboratory in Park Rapids, Minn. known as NorthStar Orthodontics, Inc. NorthStar Orthodontics provides, for example, the Porter Arch and the Quad Helix Expander.

A palatal expander is also known as a rapid palatal expander, a rapid maxillary expansion appliance, a palate expander, or an orthodontic expander. A palatal expander is used to expand the palate of a patient apart to allow the upper jaw to widen. Although the use of an expander is most common in children, it can be and has selectively been used in adults. In widening the upper jaw of the patient, the known expanders can result in physical separation of the upper jaw and can also result in a large gap between the patient's upper two front teeth.

Since the palate as a bone (the palatine processes) serves as the roof of the oral cavity as well as the floor of the nasal cavity, a significant consequence of the known expanders is that they can alter the anatomical relationship between the oral cavity and the nasal cavity. These known expanders can result in the functional disruption of the palatine processes as the anatomical barrier, causing communication between these cavities. Patients may experience pressure, pain, and headaches while wearing palatal expanders. Braces typically are used to straighten all or some of the patient's teeth after an expander has been used to widen the patient's upper jaw.

SUMMARY

The invention relates to orthodontic devices and methods for applying corrective forces within a patient's dentitions and bones known as the dento-alveolar complex (DAC) to, for example, correct the shape of the patient's palate as the geometric configuration into a proper morphologic anatomical structure of a human mouth. The patient can be a male or female human of almost any age.

The palate shaper of the invention moves teeth as one unit of the DAC into the ideal shape of human dental arch; therefore shaping the alveolar bones and palatine processes which increases the parameter of the dental arch. Thus, this orthodontic shaping device has little or no effect on the mid-palatine suture, rarely resulting in clinical symptoms of pressure, pain, headaches, or a gap between the upper two front teeth. There is little or no anatomical disruption between the oral and nasal cavities.

In one aspect, the invention relates to an orthodontic apparatus for installation in a patient's mouth. The apparatus includes a first extension wire, a second extension wire, and a palatal archwire. The first extension wire includes a proximal portion and a distal portion. The proximal portion of the first extension wire extends from a right attachment member and is manipulatable to apply a corrective buccal force on the upper right posterior DAC within the patient's palate when the apparatus is installed in the patient's mouth. The distal portion of the first extension wire extends from the proximal portion and is manipulatable to apply a corrective labial force on the upper anterior DAC and selectively a corrective buccal force on some upper left posterior DAC within the patient's palate when the apparatus is installed in the patient's mouth. The distal portion of the first extension wire terminates at a distal end. When the apparatus is installed, the distal end of the first extension is in the opposite side of the palate from the proximal portion of the first extension wire, adjacent to the proximal portion of the s second extension wire. The second extension wire includes a proximal portion and a distal portion. The proximal portion of the second extension wire extends from a left attachment member and is manipulatable to apply a corrective buccal force on the upper left posterior DAC within the patient's palate when the apparatus is installed in the patient's mouth. The distal portion of the second extension wire extends from the proximal portion of the second extension wire and is manipulatable to apply a corrective labial force on the upper anterior DAC and selectively a corrective buccal force on some right posterior DAC within the patient's palate when the apparatus is installed in the patient's mouth. The distal portion of the second extension wire terminates at a distal end, which, when installed, is in the opposite side of the palate from the proximal portion of the second extension wire; adjacent to the proximal portion of the first extension wire. The palatal archwire includes a right portion, a middle portion, and a left portion. The right portion extends from a right side of the middle portion to the right attachment member. The left portion extends from a left side of the middle portion to the left attachment member. The middle portion includes a generally M-shaped configuration that comprises a left loop, a middle loop, and a right loop. Each of the left and right loops includes a generally inverted U-shaped configuration. The middle loop includes a generally inverted a-shaped configuration. The middle portion is disposed between the first and second extension wires and a horizontal axis extending through each of the right and left attachment members. When installed in a patient's palate, the middle portion of the palatal archwire is disposed within the patient's palate. The palatal archwire is manipulatable to apply a corrective transverse force on either or both sides of the posterior DAC when the apparatus is installed in the patient's mouth.

In one embodiment according to this aspect of the invention, the first and second extension wires, the right and left attachment members, and the palatal archwire can comprise a metal alloy. The metal alloy can comprise one or more of carbon, chromium, cobalt, manganese, nickel, and stainless steel.

In another embodiment according to this aspect of the invention, each of the proximal portions can include a stem member. When installed in a patient's mouth, the stem member of the proximal portion of the first extension wire can be attached to the right attachment member to secure the apparatus. Similarly, the stem member of the proximal portion of the second extension wire can be attached to the left attachment member to secure the apparatus when the apparatus is installed in the patient's mouth.

In another embodiment according to this aspect of the invention, each of the distal portions of extension wires can traverse the upper anterior dentitions and at least some of the posterior dentitions on the opposite side of the palate. Each of the right and left attachment members can be adapted for attachment to a right clasp member and a left clasp member and each is manipulatable to apply the corrective de-rotating force independently on a molar when the apparatus is installed in the patient's palate. Each of the right and left clasp members can be mounted to an upper molar on opposite sides of the patient's palate. The palatal archwire can be elevated towards a higher portion of the palate of the patient's mouth when the apparatus is installed in the patient's mouth.

In another aspect, the invention relates to a method of applying corrective forces to the upper DAC of a patient's palate. The method includes providing an orthodontic apparatus, such as the orthodontic apparatus described above, for installation in a patient's mouth, inserting the apparatus into a palate of the patient's mouth, securing the right attachment member to a first clasp member mounted on an upper right molar, securing the left attachment member to a second clasp member mounted to an upper left molar manipulating each of the attachment members to apply the corrective de-rotating force independently on each molar, manipulating the proximal portion of the first extension wire to apply a corrective buccal force on the upper right posterior DAC, manipulating the distal portion of the first extension wire to apply a corrective labial force on at least some upper anterior DAC and selectively a corrective buccal force on at least some upper left posterior DAC, manipulating the proximal portion of the second extension wire to apply a corrective buccal force on the upper left posterior DAC, manipulating the distal portion of the second extension wire to apply a corrective labial force on at least some upper anterior DAC and selectively a corrective buccal force on at least some upper right posterior DAC, and manipulating the palatal archwire to be disposed between the first and second extension wires and a horizontal axis extending through each of the right and left attachment members and to apply a corrective transverse force on the upper DAC.

In one embodiment according to this aspect of the invention, each of the first and second extension wires, the right and left attachment members, and the palatal archwire of the orthodontic apparatus comprises a metal alloy. The metal alloy can comprise one or more of carbon, chromium, cobalt, manganese, nickel, and stainless steel.

In another embodiment, each of the proximal portions of the orthodontic apparatus includes a stem member. The step of manipulating the first stem member of the proximal portion of the first extension wire includes clasping it over the right attachment member to secure the apparatus, when the apparatus is in the patient's mouth. The step of manipulating the second stem member of the proximal portion of the second extension wire includes clasping it over the left attachment member to secure the apparatus, when the apparatus is installed in the patient's mouth.

In another embodiment, each of the distal portions of the orthodontic apparatus traverses the upper anterior dentitions and at least some of the posterior dentitions on the opposite side of the palate. The palatal archwire is elevated towards a higher portion of the palate of the patient's mouth when the apparatus is installed in the patient's mouth. Each of the manipulating steps can be repeated in order to provide a desired amount of corrective force. The middle portion of the palatal archwire can be elevated towards a higher portion of the palate of the patient's mouth when the apparatus is installed in the patient's mouth.

In another aspect, the invention relates to a device for shaping a palate. The device includes a pair of attachment members, a pair of extension wires—each protruding from one of the attachment members—and a palatal archwire spanning the attachment members. Each of the extension wires has a proximal portion attached to one of the attachment members as well as a distal portion. Each of the extension wires has a distal end. The attachment members—attached to the proximal portions of the extension wires—are generally held a distance apart from each other by the palatal archwire that is attached to each of them near its ends, leaving a middle portion spanning the area between the two attachment members. The middle portion of the palatal archwire is formed into three consecutive semi-loops that are substantially co-planar and open in alternating directions. The device is configured to be installed in a palate with the pair of attachment members attached to a pair of clasp members mounted mostly on upper first molar to independently control the rotating force inflicted upon the pair of upper first molars. The device is configured to be installed in a mouth with the middle portion of the palatal archwire in the palate—anterior to the attachment members and higher than the extension wires—to apply transverse force to the DAC. The device is configured to be installed in a patient's mouth with the pair of extension wires anterior to the attachment members with each of the proximal portions positioned to apply buccal force to the DAC. The device is configured to be installed in a patient's mouth with the distal portions of the extension wires traversed behind upper anterior dentitions to apply labial force to DAC and at least partially overlapping the proximal portion of the other extension wire to apply some buccal force to the DAC of the opposite side.

These and other objects, advantages, and features of the invention will become apparent through reference to the following description, drawings, and claims. It is noted that aspects of the embodiments described herein are not mutually exclusive and can exist in various combinations and permutations.

BRIEF DESCRIPTION OF THE DRAWINGS

In the drawings, like reference characters generally refer to the same or similar parts throughout the different views. The drawings are intended to illustrate both the details of various embodiments according to the invention as well as the principles of the invention.

DETAILED DESCRIPTION

Figure 1:
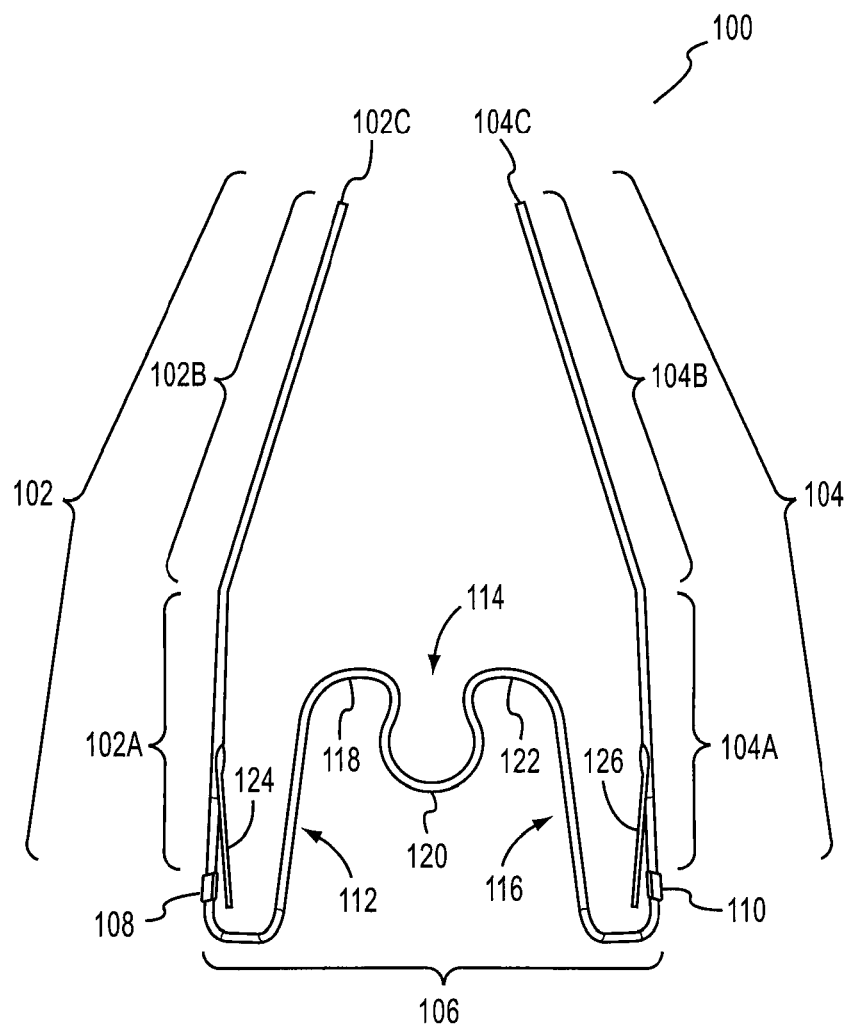
FIG. 1 is a top view of an embodiment of an orthodontic apparatus before the first and second extension wires are manipulated into a desired configuration.

In general, the invention relates to orthodontic devices and methods for applying corrective forces in three dimensions: transverse, buccal, and labial, to shape the palate within a patient's mouth.

Referring to FIGS. 1, 2, 3, 4, 5, and 6, in one embodiment according to the invention, an orthodontic apparatus 100 includes a first extension wire 102, a second extension wire 104, and a palatal archwire 106. The first extension wire 102 includes a proximal portion 102A and a distal portion 102B.

The proximal portion 102A of the first extension wire 102 extends from a right attachment member 108. The distal portion 102B of the first extension wire 102 extends from the proximal portion 102A and terminates at a distal end 102C. The second extension wire 104 includes a proximal portion 104A and a distal portion 104B. The proximal portion 104A of the extension wire 104 extends from a left attachment member 110. The distal portion 104B of the second extension wire 104 extends from the proximal portion 104A and terminates at a distal end 104C.

The first extension wire 102 and the second extension wire 104 are manipulatable such that each of the proximal portions 102A, 104A and the distal portions 102B, 104B are configured to apply corrective buccal and labial forces on DAC and teeth (not shown in Figures) when the apparatus 100 is installed in a patient's mouth. These corrective forces can be adjusted to rotate, torque, or angle the molars. For example, the distal portion 104B of the second extension wire 104 can be manipulated to overlap over the distal portion 102B and over some of the proximal portion 102A of the first extension wire 102. The precise shape chosen for the distal portions 102B and 104B will vary to suit a particular application.

The palatal archwire 106 includes a right portion 112, a middle portion 114, and a left portion 116. The right portion 112 extends from the right attachment member 108 to the right side of the middle portion 114. The left portion 116 extends from the left attachment member 110 and extends to the left side of the middle portion 114. The middle portion 114 includes a right loop 118, a middle bend 120, and a left loop 122. The middle portion 114 can be configured in a variety of configurations. In one embodiment, the middle portion 114 has a generally M-shaped configuration and each of the right loop 118 and the left loop 122 includes a generally inverted U-shaped configuration. The middle loop 120 includes a generally inverted Ω-shaped configuration.

The middle portion 114 is disposed between: the first extension wire 102; the second extension wire 104; and a horizontal axis extending through the right attachment member 108 and the left attachment member 110. Accordingly, the apparatus of the invention comprises a middle portion 114 an extension wire 102, and an extension wire 104, which—when the apparatus is installed in a patient's mouth—are each located anterior to both right attachment member 108 and left attachment member 110.

In operation, the middle portion 114 is disposed within a higher portion of the patient's palate when the apparatus 100 is installed in a patient's mouth. The palatal archwire 106 is manipulatable and configured to apply corrective transverse force on the upper DAC when the apparatus 100 is installed in a patient's mouth. These corrective forces can be adjusted unilaterally or bilaterally to rotate, torque, or angle the molars. In accordance with the invention, the three-dimensional corrective force on the patient's DAC and molars results in correction of the shape of the patient's palate.

Each of the first extension wire 102, the second extension wire 104, the right attachment member 108, the left attachment member 110, and the palatal archwire 106 can be formed from a metal alloy. The metal alloy can comprise one or more of carbon, chromium, manganese, nickel, and stainless steel. The material chosen for the apparatus 100 will vary to suit a particular application.

The apparatus 100 also includes a first stem member 124 and a second stem member 126. The first stem member 124 is disposed on the proximal portion 102A of the first extension wire 102. The second stem member 126 is disposed on the proximal portion 104A of the second extension wire 104. Each of the first stem member 124 and the second stem member 126 is configured to secure the first attachment member 108 and the second attachment member 110 when the apparatus 100 is installed in a patient's palate.

Figure 7:
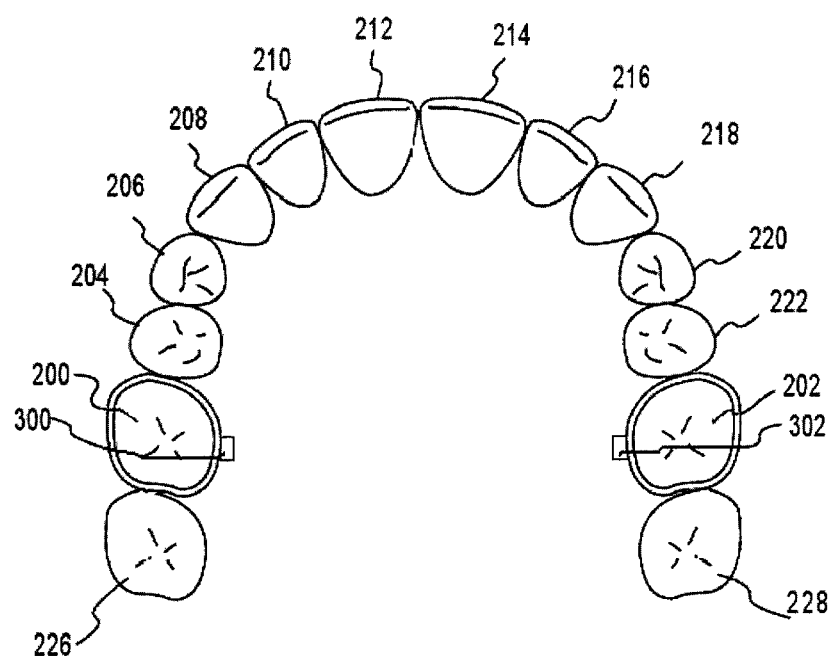
FIG. 7 is a top view of the right and left clasp members mounted on opposed molars in a patient's mouth.
Figure 8:
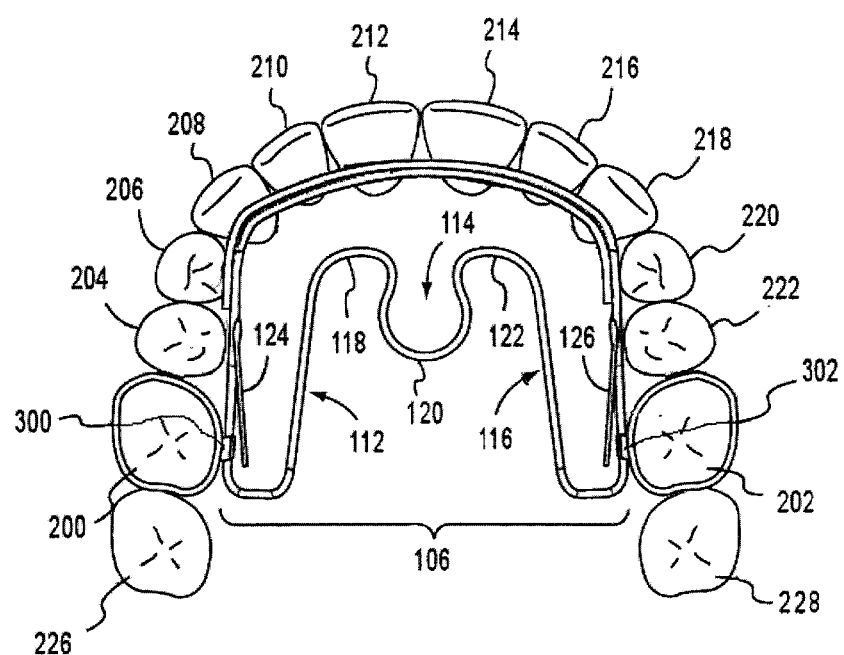
FIG. 8 is a top view of the orthodontic apparatus after the orthodontic apparatus has been installed into the patient's mouth.

Referring to FIGS. 7 and 8, the apparatus 100 also includes a right clasp member 300 and a left clasp member 302, and the clasp members are mounted onto the palatal side of preferably orthodontic molar bands. Each of the right clasp member 300 and the left clasp member 302 is adapted for attachment to the right attachment member 108 and the left attachment member 110. In operation, the right clasp member 300 is attached to an upper right first molar 200 and the left clasp member 302 is attached to an upper left first molar 202.

In one embodiment, after clasp member 300 and clasp member 302 are attached, apparatus 100 is then inserted into the palate of a patient's mouth. The right attachment member 108 is inserted into right clasp member 300, and the right stem member 124 is manipulated over the right attachment member 108 to lock. The left attachment member 110 is inserted into left clasp member 302, and the left stem member 126 is manipulated over the left attachment member 110 to lock. Each of the attachment members 108 and 110 can be manipulated to apply the corrective de-rotating force independently on each first molar 200 and 202.

By inserting right attachment member 108 into the right clasp member 300 around to upper first molar 200, the proximal portion 102A of the first extension wire 102 can be manipulated to apply corrective buccal force on the upper right posterior DAC of teeth 200, 204, and 206, and selectively right second molar 226.

By inserting left attachment member 110 into the left clasp member 302 around the upper left molar 202, the proximal portion 104A of the second extension wire 104 can be manipulated to apply corrective buccal force on the upper left posterior DAC of teeth 220, 222, and 202 and selectively left second molar 228.

The distal portion 102B of the first extension wire 102 can be manipulated to apply corrective labial force on the DAC of at least some of upper anterior dentitions 208, 210, 212, 214, and 216, and some selective corrective buccal force on teeth 218, 220, and 222. The distal portion 104B of the second extension wire 104 can be manipulated to apply corrective labial force on the DAC of at least some of upper anterior dentitions 210, 212, 214, 216, and 218; some selective corrective buccal force on teeth 208, 206, and 204.

In one embodiment of the invention, the overlapping area of distal portion 102B and distal portion 104B, when the apparatus is installed in a patient's mouth, wraps around the patient's mouth such that the overlapping area is behind teeth 206, 208, 210, 212, 214, 216, 218, and 220; selectively behind teeth 204 and 222.

In one embodiment of the invention, an operator may manipulate distal portion 102B and distal portion 104B to finely customize the corrective labial and buccal forces that those portions apply to the DAC. By having a highly customizable distal portion 102B and distal portion 104B, the apparatus provides the advantageous result of allowing an operator to provide finely-controlled and differential amounts of labial and buccal forces, precisely positioned, on individual teeth or areas of the DAC, in a patient's mouth, resulting in achieving the desired morphological anatomical structure precisely, quickly, painlessly, and efficiently.

When the apparatus is installed in a patient's mouth, some of distal portion 102B overlaps with some of proximal portion 104A, and some of distal portion 104B overlaps with some of proximal portion 102A. Accordingly, when the apparatus is installed in a patient's mouth, distal end 102C lies adjacent to proximal portion 104A, and distal end 104C lies adjacent to proximal portion 102A.

An operator of the apparatus may manipulate the palatal archwire 106 to be disposed between: the first extension wire 102; the second extension wire 104; and a horizontal axis extending through right attachment member 300 and left attachment member 302. In this disposition, palatal archwire 106 can be employed to apply corrective transverse force on either or both of the DAC of upper molars 200 and 202 and thus correct the shape of the patent's palate.

The device can be configured so that, if it is installed in a patient's mouth, each of the pair of attachment members attach to one of a pair of clasp members. As illustrated in FIG. 7, each of the clasp members 300 and 302 can be attached mostly to upper first molars 200 and 202 on the palatal sides of the mouth. As pictured in FIG. 8, the device can be configured to be attached to clasp members 300 and 302.

Figure 2:
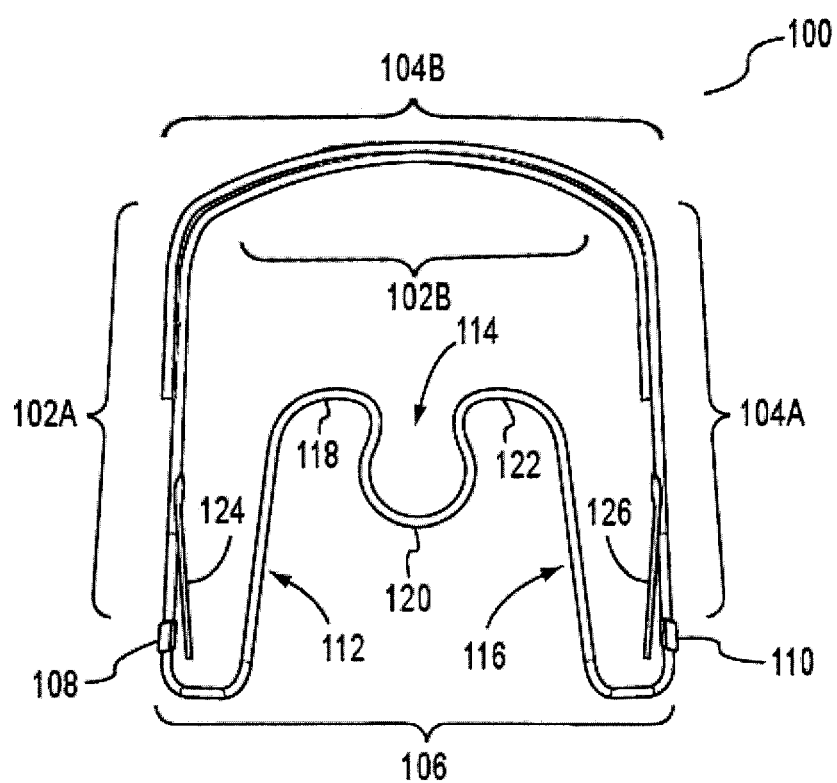
FIG. 2 is a top view of the orthodontic apparatus after the first and second extension wires are manipulated into a desired configuration.
Figure 3:
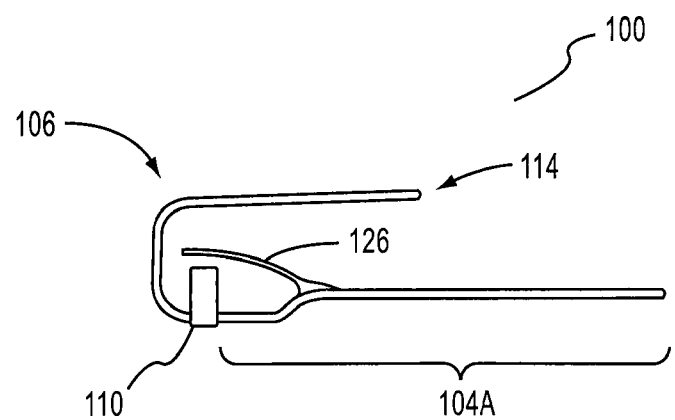
FIG. 3 is a side view of the orthodontic apparatus.
Figure 4:
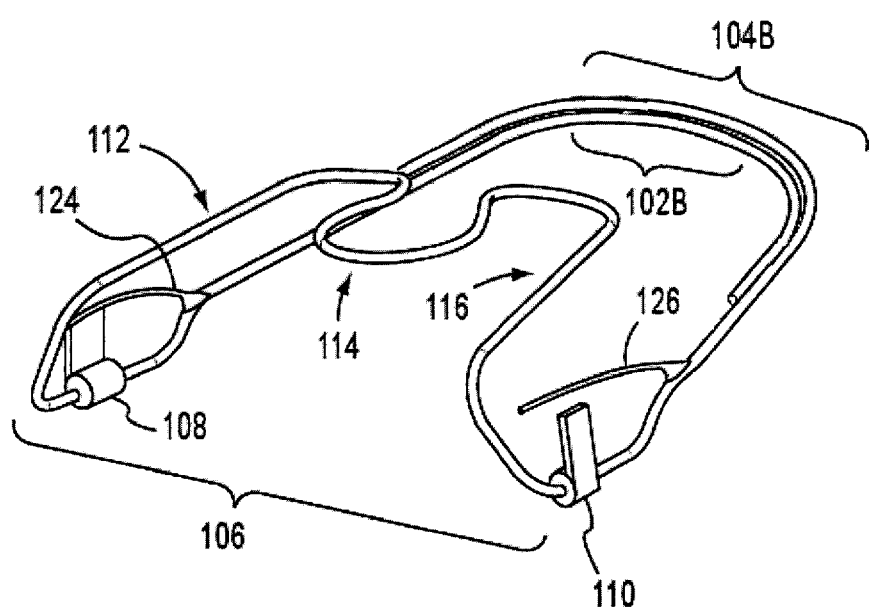
FIG. 4 is a perspective view of the orthodontic apparatus after the first and second extension wires are manipulated into a desired configuration.
Figure 5:
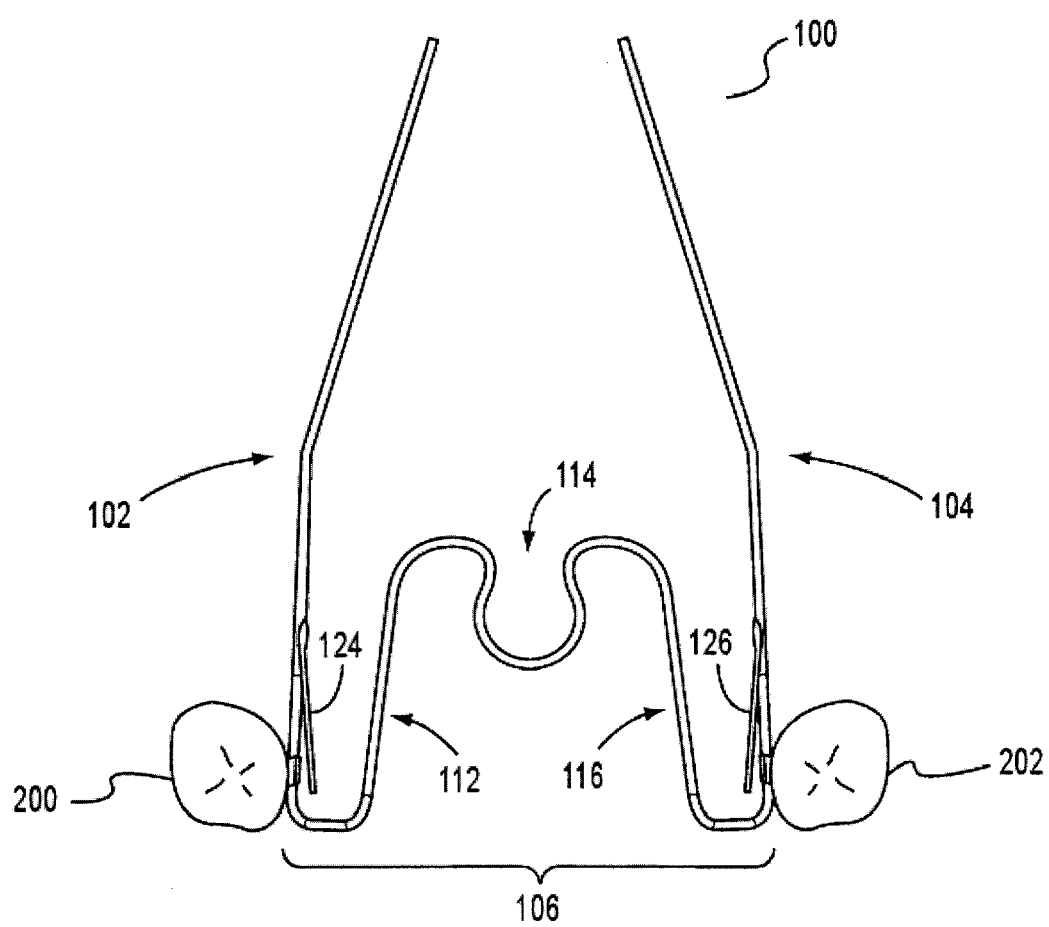
FIG. 5 is a top view of the orthodontic apparatus similar to FIG. 1 but including right and left clasp members.
Figure 6:
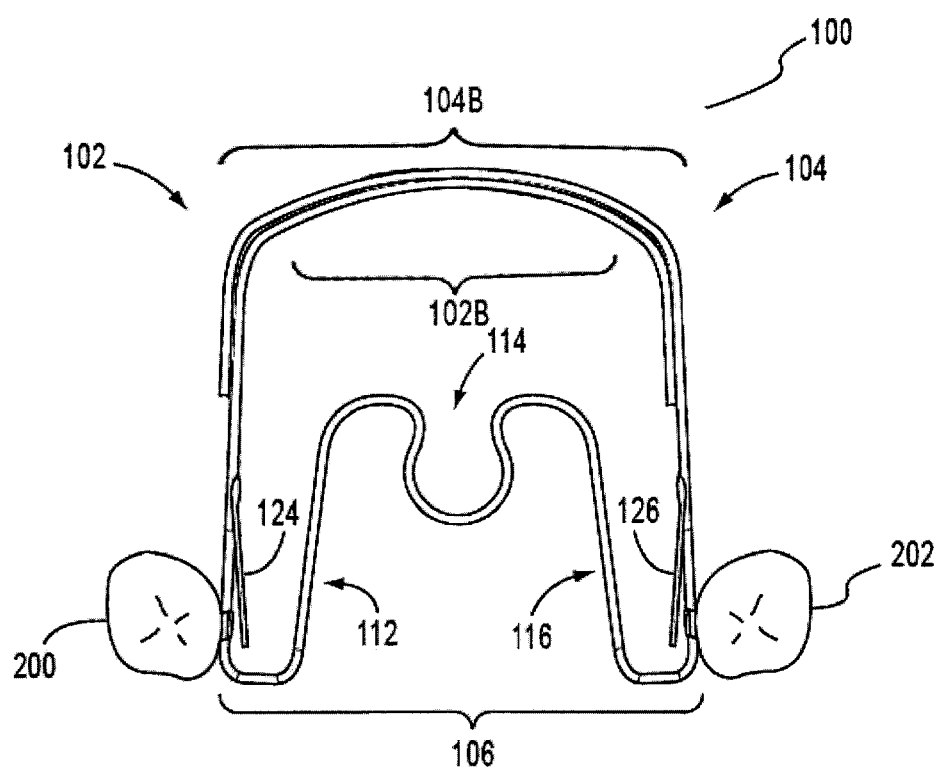
FIG. 6 is a top view of the orthodontic apparatus of FIG. 5 after the first and second extension wires are manipulated into a desired configuration.

The device is configured so that, if it is installed in a patient's mouth, the middle portion 114 of palatal archwire 106 and both of the extension wires 102 and 104 protrude in the anterior direction from the attachment members, as illustrated in FIG. 6. As illustrated in FIG. 2, if the device is installed in a patient's mouth, the middle portion of the palatal archwire is within the boundary demarcated by: proximal portion 102A; the overlapping distal portions 102B and 104B; proximal portion 104B; the axis protruding through the two attachment members 108 and 110. As illustrated in FIG. 4, the middle portion of the palatal archwire is higher than the extension wires so that it will be positioned in the patient's palate. An operator may advantageously employ this aspect of this configuration of the invention to cause bilateral or unilateral transverse force to be applied to the DAC.

The invention of the present disclosure provides a novel apparatus and method of treatment to: increases the dental arch parameter by shaping the patient's palate into a morphologically corresponding geometry of human mouth; independently rotate, torque, apply transverse, buccal and labial forces to the upper anterior and upper posterior regions of the DAC; shape the alveolar processes; and shape the palatine processes. Aspects of the apparatus function to move teeth as a single unit of the dento-alveolar complex and increase the parameter of the dental arch. Operation and use of the apparatus has little or no effect on the mid-palatine suture, and results in little or no anatomical disruption between the oral and nasal cavities By supplying these functions in a single apparatus, the apparatus provides the advantageous result of allowing an operator to provide finely controlled and differential amounts of transverse, buccal, and labial force, precisely positioned, on individual teeth or areas of the DAC, in a patient's mouth, resulting in achieving the desired geometric configuration of morphologic anatomical structure precisely, quickly, painlessly, and efficiently.

Various modifications may be made to the embodiments disclosed herein. The disclosed embodiments and details should not be construed as limiting but instead as illustrative of some embodiments and the principles of the invention.

What is claimed is:

1. An apparatus for applying forces within a mouth of a patient, the apparatus comprising:
   a right portion with a proximal end and a distal end;
   a left portion with a proximal end and a distal end, distalmost ends of the right portion and the left portion overlapping one another; and
   a middle portion, the middle portion being engaged with the right portion and the left portion at points closer to the proximal ends of the right and left portions than the distal ends of the right and left portions,
   wherein the middle portion includes a right loop, a left loop, and a middle loop between the right loop and the left loop, the middle loop being oriented toward the distal ends of the right and left portions, the right and left loops being oriented in an opposite direction to the middle loop.

2. The apparatus of claim 1, wherein the middle portion is adjustable.

3. The apparatus of claim 1, wherein the right and left portions are wires, and the middle portion is a palatal archwire.

4. The apparatus of claim 1, wherein one of the distal ends of the right portion or the left portion overlaps a majority of the other right or left portion.

5. The apparatus of claim 1, wherein the right portion engages the middle portion at a right attachment member, and
   the left portion engages the middle portion at a left attachment member.

6. The apparatus of claim 5, further comprising:
   a right stem engaging the right portion and configured to lock to the right attachment member; and
   a left stem engaging the left portion and configured to lock to the left attachment member.

7. The apparatus of claim 6, further comprising:
   a right clasp configured to engage a first molar in a patient's mouth and configured to engage the right attachment member; and
   a left clasp configured to engage a second molar in a patient's mouth and configured to engage the left attachment member.

8. The apparatus of claim 1, wherein the proximal ends of the right and left portions and the distal ends of the right and left portions are configured to apply corrective forces to rotate, torque, or angle molars when installed in a patient's mouth.

9. The apparatus of claim 1, wherein the apparatus is formed from a metal alloy.

10. The apparatus of claim 9, wherein the metal alloy includes at least one of carbon, chromium, manganese, nickel, and stainless steel.

11. The apparatus of claim 1, wherein the middle portion has an approximately M-shaped configuration.

12. The apparatus of claim 1, wherein the middle loop of the middle portion has an approximately Ω-shaped configuration.

13. The apparatus of claim 1, wherein one of the distal ends of the right or left portions overlaps the other right or left portion such that the middle loop of the middle portion, the distal end of the right portion, and the distal end of the left portion are oriented in the same direction.

\* \* \* \* \*